United States Patent [19]

Payne

[11] 4,381,159

[45] Apr. 26, 1983

[54] MAGNETIC FINGERPRINT DUSTING BRUSH

[75] Inventor: John M. Payne, Maxey, England

[73] Assignee: Sirchie Fingerprint Laboratories, Inc., Raleigh, N.C.

[21] Appl. No.: 206,304

[22] Filed: Nov. 12, 1980

[51] Int. Cl.³ .............................................. A61B 5/10
[52] U.S. Cl. .................................. 401/118; 118/31.5; 427/1
[58] Field of Search ................ 401/13, 118, 129, 191, 401/292; 427/1; 118/31.5; 15/1.5 A

[56] References Cited

U.S. PATENT DOCUMENTS

| | | | |
|---|---|---|---|
| 3,132,036 | 5/1964 | MacDonell | 118/31.5 |
| 3,549,397 | 12/1970 | McDonald | 427/1 |
| 3,831,552 | 8/1974 | Schmidt et al. | 118/31.5 |
| 3,870,186 | 3/1975 | Reinhard | 401/129 |
| 3,897,749 | 8/1975 | Maz et al. | 118/31.5 |

FOREIGN PATENT DOCUMENTS 52-2000  1/1977  Japan ..................................... 427/1

Primary Examiner—William Pieprz
Attorney, Agent, or Firm—Edward M. Farrell

[57] ABSTRACT

A magnetic fingerprint dusting brush comprising a handle (10) incorporating a projecting magnet (14) at one end, and a powder cartridge which is a push fit onto the handle, said cartridge comprising a shroud (16), which includes an inner blind sleeve (18) which extends coaxially from an inner cylindrical sleeve (20) of larger diameter, whereby the section (18) receives the magnet (14) and section (20) receives the lower end of the handle (10) when the cartridge is fitted in place on the handle, and a cap (24) which assembles with the shroud (16) to form a reservoir around the shrouded magnet containing a measured quantity of ferrous powder particles (26) carrying dusting powder which align on the shrouded magnet to form a bristle like array (28) exposed when the cap (24) is removed.

7 Claims, 3 Drawing Figures

MAGNETIC FINGERPRINT DUSTING BRUSH

FIELD OF INVENTION

This invention concerns brushes for dusting surfaces believed to bear fingerprints, hereinafter referred to as magnetic fingerprint dusting brushes.

BACKGROUND TO THE DISCLOSURE

Magnetic fingerprint dusting brushes have been used for some time by various police forces in the process of dusting for fingerprints at the scene of a crime.

A known brush has a handle similar to the handle of a conventional artist's brush but carrying a small cylindrical permanent magnet instead of bristles. In use, the magnet is dipped into a jar of ferrous powder which is mixed with a quantity of powdered carbon or the like dusting powder. The ferrous powder clings to the magnet along the lines of force of the magnetic field and forms a bristle-like array which serves as a carrier for the dusting powder. The magnetic brush is then used in place of a conventional brush to locate and identify latent fingerprints, the dusting powder transferring from the aligned ferrous powder particles to the print area.

In the known art, the loading of a 'magnetic brush' and the subsequent unloading after use can be a messy procedure. Some prior art magnetic brushes have a retractable magnet within a non-ferrous blind sleeve, so that when the magnet is retracted the ferrous powder is intended to be forced to drop off, for example into a storage jar. However, a residue of carbon powder often remains on the sleeve, so that it still has to be cleaned properly before it can be stored, as for example in the user's pocket.

OBJECTS OF THE INVENTION

It is a primary object of the present invention to provide an improved magnetic fingerprint dusting brush which inter alia overcomes the aforementioned problems of loading and unloading.

Further objects of the invention are:

spatially to separate powder loading from the magnetic field;

to keep the magnet clean and free from powder;

to facilitate use of different powder mixtures;

to minimise risk of spillage due to open powder containers;

to avoid problems associated with trying to get the correct amount of powder on brush—the invention enables a measured amount of powder mixture to be pre-loaded in a cartridge;

to avoid messy residues remaining on the handle after use—the brush handle need never come into contact with powder with the arrangement of this invention;

to minimise 'dilution' of the powder. With conventional arrangements the dusting powder is gradually used up, so that the efficiency deteriorates over a period. The invention provides a cartridge which is disposable when the dusting powder content is spent.

BRIEF SUMMARY OF THE INVENTION

According to the present invention a magnetic fingerprint dusting brush comprises:

a handle which is magnetised at least at one end or includes a magnet at one end thereof, a non-magnetic shroud adapted to be secured to the magnet or the magnetic end of the handle, a cover detachably secured to the shroud and forming when secured on the shroud an enclosed powder reservoir, and a mixture of ferrous and dusting powder in the reservoir, the ferrous powder aligning along the lines of the magnetic field of the magnet to form the known magnetic bristles when the magnet or magnetised end of the handle is inserted in the shroud.

FURTHER FEATURES OF THE INVENTION

Typically the handle is like a pen and a small cylindrical magnet is fitted into the end in place of a pen-nib. The shroud is likewise cylindrical and is adapted to be push-fitted over the magnet handle so that it can be easily pushed into place or removed. The shroud includes an inner cylindrical sleeve closed at its lower end, which sleeve is the part into which the magnet/handle fits and an outer cylindrical sleeve, of somewhat larger diameter, extends around the inner sleeve to form therewith an annular space, the lower end being open and the upper end closed, and the cover is in the form of a closed cylindrical cap of similar transverse dimensions to the outer sleeve portion of the shroud and adapted to be secured thereto. The inner sleeve extends axially beyond the outer sleeve so that, when the cap is removed, it is exposed like a pen-nib.

Although the inner sleeve is formed from non-magnetic material such as a plastics material, it assumes the properties of a magnet when the magnet or magnetic end of the handle is inserted therein. Consequently, magnetic particles contained in the reservoir will cling to the outer surface of the inner sleeve in the same way as if it were a magnet to form magnetic bristles in the aforementioned manner.

One advantage of the invention is that the shroud and detachable cover/cap can be formed entirely from non-magnetic material (and are preferably so formed to create a non-magnetic cartridge) and the mixture of magnetisable ferrous powder and dusting powder can be loaded into and unloaded from the cartridge with the cartridge separate from the handle, and away from the effect of the magnetic field associated therewith.

Another even more important advantage of the invention is that the permanent magnet need never come into contact with the powder so that the magnet remains clean at all times. Thus, after use, the cover or cap can be replaced and the cartridge removed from the handle. The latter can then be put directly into the pocket without any need for cleaning. To this end the handle conveniently includes a pocket clip or the like.

A further advantage of the invention is that a number of separate cartridges can be carried by a user, containing different powder mixtures for different types of fingerprint detection, and there is no need for elaborate cleaning procedures when the user wishes to change from using one type of powder mixture to another.

A non-magnetic cover may be provided for fitting over the magnet or magnetic handle when a cartridge is not in position.

DESCRIPTION OF EMBODIMENT

Figure 2:
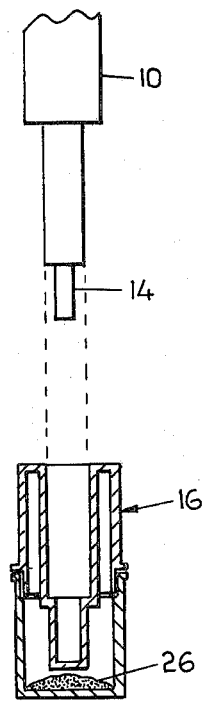
FIG. 2 shows the magnet withdrawn from the cartridge.

The magnetic fingerprint dusting brush has a plastics tubular barrel or handle 10 including a pocket clip 12 and, as best shown in FIG. 2, a magnet 14 which projects from one end. A powder cartridge includes a shroud, generally identified by reference numeral 16, which is detachably securable to the handle by a simple push-fit. The shroud 16 includes a blind sleeve portion 18 which extends coaxially from a cylindrical inner sleeve portion 20 of larger diameter. The portion 18 closely shrouds the magnet 14 when the cartridge is fitted in place on the handle by pushing the portion 20 over the lower end of the handle 10.

The upper end of the inner sleeve portion 20 is integral with a cylindrical outer sleeve 22 which extends from its upper end by the same axial length as the inner sleeve portion 20. The cartridge also includes a cylindrical cap 24 which is adapted to be screwed to the open end of the outer sleeve 22. When the cap 24 is unscrewed and removed, the inner sleeve portion 18 is exposed. Both the shroud 16 and the cap 24 are made of plastics or other suitable non-magnetisable material.

Figure 1:
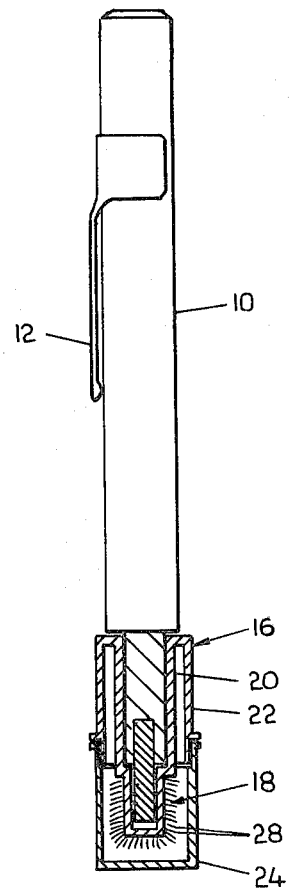
FIG. 1 is a cross-section through one embodiment of the invention.
Figure 3:
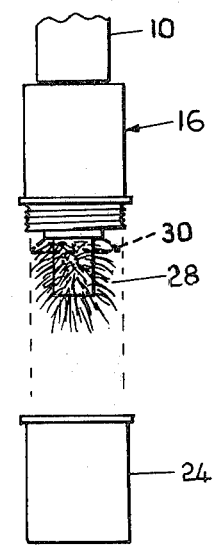
FIG. 3 shows the cartridge end of the brush with the cap-cover removed, ready for use.

The cap 24 contains a measured quantity of ferrous powder particles 26 (see FIG. 2) which, when the magnet 14 is inserted into the sleeve portion 18, are attracted to the sleeve portion 18 and align with the magnetic field to form a bristle-like array 28 as shown in FIGS. 1 and 3. Mixed with the particles 26 are carbon black particles or the like forming a fingerprint dusting powder, which particles are carried by the bristle-like array of ferrous particles in known manner. Removing the cap 24 exposes the loaded "bristles" as shown in FIG. 3; the brush is then ready for use.

After use the cap 24 can be screwed onto the shroud 16 and the cartridge can, if required, then be removed from the handle 10. A non-magnetic cover (not shown, but taking the form of a simple cylindrical blind sleeve) may be fitted over the projecting magnet 14 or over the entire lower end of the handle when the handle is not assembled with a cartridge.

A further refinement may be provided in the form of a frusto-conical guard 30 at the junction of the inner sleeve portion 18 and the shoulder between it and the larger diameter inner sleeve portion 20. This guard 30 serves to prevent powder particles from becoming trapped between the screw threaded section of the shroud 16 and the cap 24 when the latter is fitted to the shroud over the bristle-like array 28 after use.

Apart from the aforementioned advantages of the invention, it is apparent that the user may readily carry a plurality of exchangeable cartridges containing powders of different formations for differing fingerprinting circumstances and techniques.

Clearly, the invention is not restricted to the embodiment hereinbefore described with reference to the drawings. For example, the magnet can be formed as an integral part of the handle structure, thereby making possible a simple construction of shroud, such as a simple sleeve having a flanged lower end, to which flange the cover or cap is securable to define a closed powder reservoir around the magnet. Further modifications will occur to those skilled in the art, all generally in accordance with the spirit and scope of the invention which will be clear from the preceding description.

I claim:
1. A magnetic fingerprint dusting brush comprising:
   (a) a handle which incorporates a magnet portion projecting at one end thereof;
   (b) a non-magnetic shroud adapted to be assembled with the handle closely to shroud the projecting magnet portion;
   (c) said shroud including an inner blind sleeve for closely shrouding the magnet portion and an outer sleeve to which a cover is adapted to be detachably secured;
   (d) said inner sleeve having a first portion of greater cross-section for assembly with the handle and a coaxial second portion of lesser cross-section connected to the first portion through a shoulder for closely shrouding the magnet portion;
   (e) a cover detachably securable to the handle/-shroud assembly to form in its secured position an enclosed powder reservoir around the shrouded magnet portion;
   (f) said shroud and cover constituting a powder cartridge for assembly with the handle; and
   (g) a mixture of ferrous and dusting powder in the reservoir.
2. A magnetic fingerprint dusting brush according to claim 1, and further comprising a powder guard on the inner sleeve in the region of said shoulder.
3. A magnetic fingerprint dusting brush according to claim 1 wherein the shroud and cover or cap are both formed entirely of non-magnetisable material.
4. A magnetic fingerprint dusting brush comprising:
   (a) a non-magnetic handle fitted with a projecting cylindrical magnet at one end;
   (b) a cylindrical powder cartridge for assembly with said handle around the magnet, said cartridge comprising:
      (i) a non-magnetic cylindrical shroud detachably securable to the handle to shroud the magnet and which is a push fit into its shrouding position around said magnet;
      (ii) a non-magnetic cover comprising a cylindrical cap detachably securable to the shroud to form therewith an enclosed powder reservoir around the shrouded magnet and which is a powder-tight fit on said shroud.
5. A magnetic fingerprint dusting brush according to claim 4, wherein the cap is a screw fit on to the shroud.
6. A magnetic fingerprint dusting brush according to claim 5, wherein the shroud has an inner sleeve for shrouding the magnet and an externally screwthreaded outer sleeve for cooperating with an internally screwthreaded cap.
7. A magnetic fingerprint dusting brush according to claim 6, wherein the inner sleeve of the shroud has a portion of greater diameter which is a push fit on the handle and a portion of lesser diameter for shrouding the projecting magnet.

* * * * *